United States Patent
Ueda et al.

(10) Patent No.: US 7,463,563 B2
(45) Date of Patent: Dec. 9, 2008

(54) DEFICIENCY DETECTING APPARATUS FOR OPTICAL DISK

(75) Inventors: Eiji Ueda, Yawata (JP); Takashi Kishimoto, Nara (JP); Shin-ichi Yamada, Katano (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 18 days.

(21) Appl. No.: 10/521,630

(22) PCT Filed: Sep. 17, 2003

(86) PCT No.: PCT/JP03/11808

§ 371 (c)(1),
(2), (4) Date: Jan. 19, 2005

(87) PCT Pub. No.: WO2004/027405

PCT Pub. Date: Apr. 1, 2004

(65) Prior Publication Data

US 2006/0164939 A1    Jul. 27, 2006

(30) Foreign Application Priority Data

Sep. 20, 2002    (JP) .............................. 2002-274532

(51) Int. Cl.
   G11B 5/09    (2006.01)

(52) U.S. Cl. ................ 369/47.5; 369/44.32; 369/53.15; 369/44.34; 369/116

(58) Field of Classification Search .............. 369/53.15, 369/53.26, 47.5, 116, 53.32, 53.27, 44.32, 369/44.34

See application file for complete search history.

(56) References Cited

U.S. PATENT DOCUMENTS

| 4,719,621 | A | * | 1/1988 | May ........................... 370/402 |
| 4,785,295 | A | * | 11/1988 | Fukui et al. .................. 340/679 |
| 5,126,994 | A | * | 6/1992 | Ogawa et al. ............... 369/116 |
| 5,184,343 | A | * | 2/1993 | Johann et al. ............ 369/53.15 |
| 5,210,735 | A |   | 5/1993 | Hoshino et al. |

(Continued)

FOREIGN PATENT DOCUMENTS

JP    60-107749 A    6/1985

(Continued)

OTHER PUBLICATIONS

Translation of JP Patent No. 61-145743.*

*Primary Examiner*—Wayne Young
*Assistant Examiner*—Linh T Nguyen
(74) *Attorney, Agent, or Firm*—Hamre, Schumann, Mueller & Larson, P.C.

(57) ABSTRACT

The present invention provides a deficiency detecting apparatus that can accurately detect dusts and deficiencies on an optical disk even when an emitting power of a laser light source changes. The deficiency detecting apparatus is provided with a deficiency detecting section for detecting deficiencies or the like on an optical disk by reflected light, and a power adjusting section for adjusting an emitting power of a laser light source to be an optimum value. The deficiency detecting section can accurately detect the deficiencies on the optical disk even when the laser power changes by comparing a threshold value, which is determined in accordance with the adjustment result of the power adjusting section, with a value in accordance with the reflected light.

12 Claims, 9 Drawing Sheets

U.S. PATENT DOCUMENTS

| | | | |
|---|---|---|---|
| 5,218,589 A | | 6/1993 | Aoki |
| 5,471,449 A | * | 11/1995 | Kaneko et al. ............ 369/53.17 |
| 5,485,444 A | * | 1/1996 | Kuhn et al. .............. 369/53.15 |
| 5,559,785 A | * | 9/1996 | Honda et al. ............. 369/59.12 |
| 5,872,763 A | * | 2/1999 | Osakabe ................. 369/47.53 |
| 6,061,316 A | * | 5/2000 | Nakamura et al. ....... 369/47.53 |
| 6,215,741 B1 | * | 4/2001 | Ishiduka ................. 369/44.34 |
| 6,621,779 B1 | * | 9/2003 | Inokuchi et al. .......... 369/47.51 |
| 6,654,329 B1 | * | 11/2003 | Kondo et al. ............. 369/53.27 |
| 6,842,412 B2 | * | 1/2005 | Ushiyama et al. ........ 369/47.53 |
| 7,039,835 B2 | * | 5/2006 | Hodkinson et al. ............ 714/42 |
| 7,085,210 B2 | * | 8/2006 | Ogawa .................... 369/47.53 |
| 2002/0034137 A1 | | 3/2002 | Okumura et al. |
| 2003/0133378 A1 | * | 7/2003 | Kawashima et al. ..... 369/47.53 |

FOREIGN PATENT DOCUMENTS

| | | |
|---|---|---|
| JP | 61-145743 A | 7/1986 |
| JP | 3-083235 A | 4/1991 |
| JP | 9-115142 A | 5/1997 |
| JP | 9-147359 | 6/1997 |
| JP | 9-282658 | 10/1997 |
| KR | 2002-0022604 | 3/2002 |

* cited by examiner

DEFICIENCY DETECTING APPARATUS FOR OPTICAL DISK

TECHNICAL FIELD

The present invention relates to a deficiency detecting apparatus applied to a recording-reproducing apparatus which records and reproduces an information signal with respect to an information medium using laser light from a semiconductor laser or the like.

BACKGROUND ART

Generally, when information is recorded on an information medium (hereinafter, called an optical disk) using laser light, tracking control is performed by detecting a positional deviation of a light spot on the optical disk from a desired track using reflected light from the optical disk and by driving an objective lens in accordance with the detection signal so that the light spot can scan on the desired track.

If, however, an optical disk has a dust attached thereon or a defect (hereinafter, generically called a deficiency) in an information layer thereof, the accurate reflected light from the optical disk cannot be obtained, and thus the accurate tracking control is difficult to perform. When a trouble occurs in the tracking control, a problem that laser light is irradiated to the outside of an area to be recorded accordingly may occur.

In order to avoid the above problem, a method for detecting deficiencies on an optical disk from a change in the reflected light has been utilized conventionally. This method makes use of a phenomenon that the amount of the reflected light decreases when a deficiency lies on the optical disk. That is, the deficiencies on the optical disk can be detected by comparing the amount of the reflected light from the optical disk with a predetermined threshold value.

However, when recording information onto the optical disk, an optimum emitting power of a laser light source depends on the temperature of the optical disk or the like, and thus it is necessary to adjust the emitting power of the laser light source to an optimum value at a required time. Meanwhile, when the emitting power of the laser light source changes, the amount of the reflected light from the optical disk accordingly changes. Thus, it was found out that deficiencies on the optical disk were not able to be detected accurately by the conventional configuration for detecting deficiencies on the optical disk, in which the amount of reflected light from the optical disk is compared with the predetermined threshold value.

In light of the above-stated problems, another technique for detecting deficiencies on an optical disk is proposed, which includes the following means: a means for irradiating an information track configured on the optical disk with laser light via an optical system and receiving the reflected light from the information track using a photodetector so as to check the deficiencies on a recording track, thereby detecting average reflected light from the information track; and a detection controlling means for controlling the means for detecting the deficiencies on the information track in accordance with the average reflected light (see, for example, JP60 (1985)-107749A, P.3 lower right column line 15-P.4 upper right column line 1, and FIG. 3). Using this technique, the change of the reflected light is detected by assuming the average value of the reflected light as a threshold value. Thus even when the amount of the reflected light changes, the deficiencies on the optical disk can be detected regardless of the amount of the reflected light.

According to the above configuration, however, since the deficiencies on the optical disk are detected using the average reflected light, problems in detecting the deficiencies on the optical disk may occur because of the incapability of responding to the abrupt change of the emitting power of the laser light source, for example, when switching from a reproducing mode to a recording mode. That is, more specifically, when the deficiency is present on the optical disk immediately after the switching from the reproducing mode to the recording mode, it is hard to detect the deficiency, and the tracking control is negatively affected, thereby the light beam is applied to the outside of an area to be recorded.

DISCLOSURE OF THE INVENTION

In light of the above-stated problems, it is an object of the present invention to provide an apparatus that can detect deficiencies on an optical disk accurately even when an emitting power of a laser light source changes.

In order to attain the above-mentioned object, a first deficiency detecting apparatus of the present invention detects deficiencies on an information medium that are unable to be recorded or reproduced when an information signal is recorded/reproduced with respect to the information medium using a light beam generated by a laser light source. The first deficiency detecting apparatus includes a power adjusting section for adjusting an emitting power of the laser light source to an optimum value; and a deficiency detecting section for comparing a threshold value determined in accordance with the emitting power of the laser light source adjusted by the power adjusting section with a value corresponding to reflected light that is the light beam reflected by an information layer of the information medium, and detecting the deficiencies on the information layer in accordance with a result of the comparison.

With this configuration, a deficiency such as a dust and a defect on the information layer of the information medium can be detected accurately, even when the emitting power of the laser light source changes.

In the first deficiency detecting apparatus of the present invention, for simplicity of the configuration of the deficiency detecting section, it is preferable to adopt any one of the following configurations: the deficiency detecting section determines the threshold value in accordance with the emitting power selected from a predetermined range of laser power; determines the threshold value in accordance with an average value of the emitting power adjusted by the power adjusting section; determines the threshold value in accordance with a value obtained by summing at predetermined rates plural power levels, for each of which an emitting power is determined selectively; determines the threshold value in accordance with the highest power level among the plural power levels, for each of which an emitting power is determined selectively; and determines the threshold value in accordance with an erasing power level that is used for erasing among the plural power levels, for each of which an emitting power is determined selectively.

Moreover, in order to attain the above-mentioned object, a second deficiency detecting apparatus of the present invention detects deficiencies on an information medium that are unable to be recorded or reproduced when an information signal is recorded/reproduced with respect to the information medium using a light beam generated by a laser light source. The second deficiency detecting apparatus includes a power adjusting section for adjusting an emitting power of the laser light source to an optimum value, and a deficiency detecting section for amplifying a signal corresponding to reflected light that is the light beam reflected by an information layer of the information medium at an amplification factor determined in accordance with the emitting power of the laser light source adjusted by the power adjusting section so as to generate a signal for amplified reflected light amount, and for comparing a value corresponding to the signal for the amplified reflected light amount with a predetermined threshold value and for detecting the deficiencies on the information layer in accordance with a result of the comparison.

With this configuration, a deficiency such as a dust and a defect on the information layer of the information medium can be detected accurately, even when the emitting power of the laser light source changes.

In the second deficiency detecting apparatus of the present invention, for simplicity of the configuration of the deficiency detecting section, it is preferable to adopt any one of the following configurations: the deficiency detecting section determines the amplification factor in accordance with an emitting power selected from a predetermined range of laser power; determines the amplification factor in accordance with an average value of the emitting power adjusted by the power adjusting section; determines the amplification factor in accordance with a value obtained by summing at predetermined rates the plural power levels, for each of which an emitting power is determined selectively; determines the amplification factor in accordance with the highest power level among the plural power levels, for each of which an emitting power is determined selectively; or determines the amplification factor in accordance with an erasing power level that is used for erasing among the plural power levels, for each of which an emitting power is determined selectively.

BEST MODE FOR CARRYING OUT THE INVENTION

Preferred embodiments of the present invention are described below in detail exemplifying a phase-change type optical disk with reference to the drawings. In the following embodiments, a laser power is assumed to have plural levels because of exemplifying a phase-change type optical disk, but the technical thought of the present invention can be applied similarly when the laser power is a single laser power or an analog type one.

Embodiment 1

Figure 1:
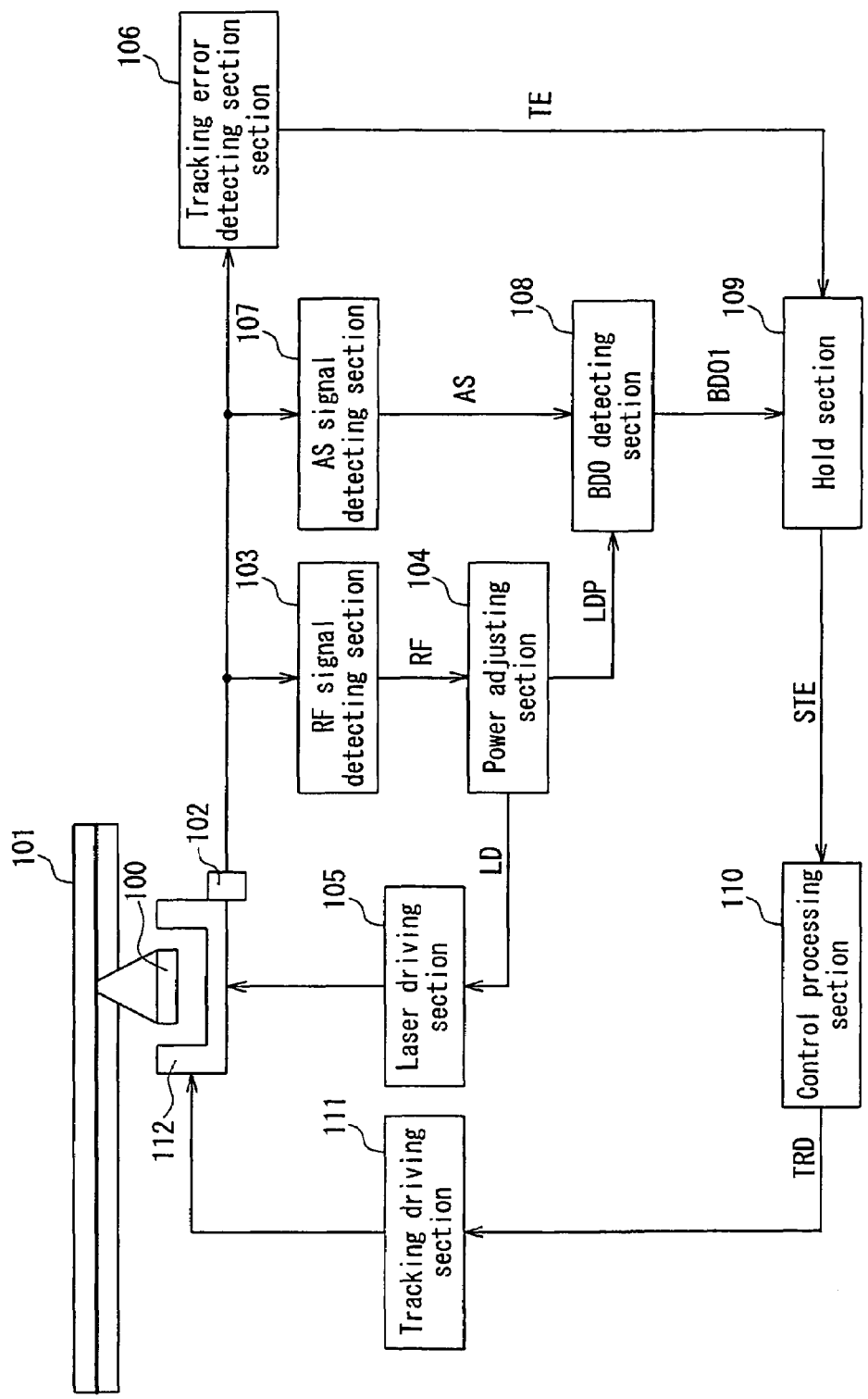
FIG. 1 is a block diagram showing an example of the configuration of the deficiency detecting apparatus according to Embodiment 1 of the present invention.

FIG. 1 is a block diagram showing an example of the configuration of a deficiency detecting apparatus according to Embodiment 1 of the present invention. In FIG. 1, a light beam irradiated from a laser light source 100 to an information layer of an optical disk 101 is reflected by the information layer, and the reflected light is detected by a photodetector 102. A tracking error detecting section 106 outputs a tracking error signal TE in accordance with the positional deviation of a light beam on the optical disk 101 from a track on which the information layer is formed, using a detecting signal from the photodetector 102 provided with a photodetecting element that is divided into plural parts.

A hold section 109 receives the tracking error signal TE from the tracking error detecting section 106 and a below-described hold signal BDO1, performs hold processing to the tracking error signal TE in accordance with the hold signal BDO1, and subsequently outputs a servo tracking error signal STE. More specifically, the hold section 109 outputs the tracking error signal TE as the servo tracking error signal STE when the hold signal BDO1 is "L" (here, "L" denotes a lower level of a voltage), and outputs a zero signal as the servo tracking error signal STE when the hold signal BDO1 is "H" (here, "H" denotes a higher level of a voltage).

A control processing section 110 receives the servo tracking error signal STE, performs phase-lead compensation processing, and subsequently outputs the servo tracking error signal STE as a tracking driving signal TRD. A tracking driving section 111 performs tracking control by supplying an electric power in accordance with the tracking driving signal TRD to a tracking actuator 112 and driving an objective lens in the tracking actuator 112.

In short, a tracking controlling section is composed of the photodetector 102, the tracking error detecting section 106, the hold section 109, the control processing section 110, the tracking driving section 111 and the tracking actuator 112, and a tracking control is performed so that a light beam on the optical disk 101 can scan on a desired track.

A reproducing signal detecting section (hereinafter, called a RF signal detecting section) 103 in FIG. 1 receives a detecting signal from plural photodetecting elements of the photodetector 102, and outputs a reproducing signal RF that corresponds to the information recorded on the optical disk 101. A power adjusting section 104 receives the reproducing signal RF from the RF signal detecting section 103, and outputs an emitting power instruction LD for the laser light source 100 such as a semiconductor laser so that the reproducing signal RF can be optimum. More specifically, a signal that is recorded on the optical disk 101 in accordance with a predetermined emitting power instruction LD for the laser light source 100 is reproduced, whereby the emitting power instruction LD for the laser light source 100, which provides the optimum reproducing signal RF during recording, can be sought (here, 'optimum' refers to the reproducibility of the recorded data, and, for simplicity, the 'optimum' is assumed to be a state in which the jitter of the reproducing signal RF is minimum).

Figure 2:
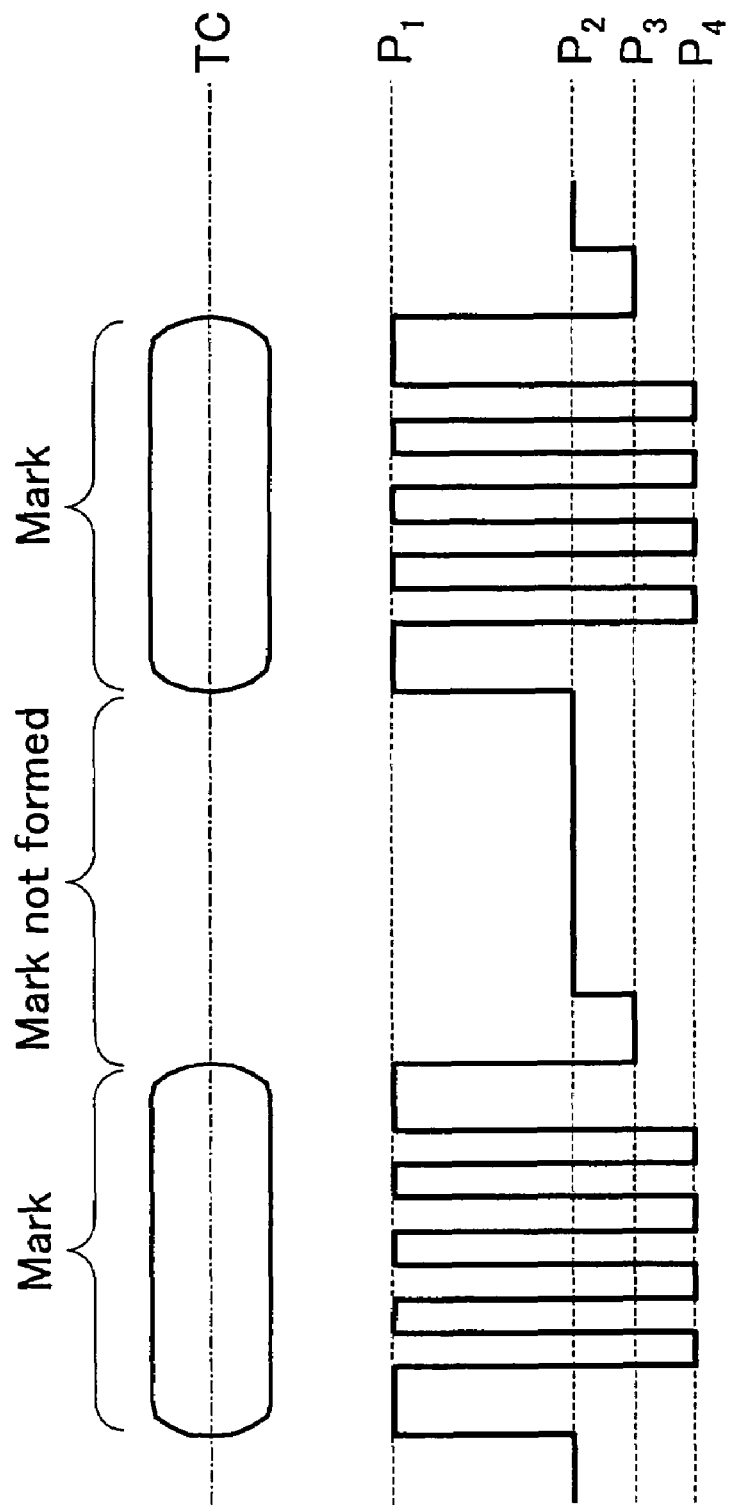
FIG. 2 is a diagram showing an example of the emitting power instruction for the laser light source according to Embodiment 1 of the present invention.

FIG. 2 shows an example of the emitting power instruction LD for the laser light source 100. In FIG. 2, the horizontal axis indicates time, the upper portion in FIG. 2 illustrates a pattern of a recorded mark formed along a track center line (TC) on the optical disk 101, and the lower portion in FIG. 2 illustrates the output pattern of the emitting power instruction LD for the laser light source 100, which corresponds to the recorded mark. In FIG. 2, the emitting power instruction LD for the laser light source 100 is composed of four emitting power levels of P1, P2, P3 and P4. Here, the emitting power level P1 is the highest value of the emitting power of the laser light source, the emitting power level P2 is the emitting power level for erasing the mark, and the emitting power levels P3 and P4 are determined so as to obtain the recorded mark with a desired shape. Generally, when the value of the emitting power instruction LD is smaller than the optimum value, there is a problem that the mark cannot be formed onto the optical disk 101, and when the value of the emitting power instruction LD is larger than the optimum value, there is a problem that the information on the adjacent track is negatively affected. Also, the optimum value changes depending upon the temperature of the optical disk 101.

The power adjusting section 104 in FIG. 1 obtains an average value of the emitting power instruction LD by the weighted summation of the four levels of the emitting power, and outputs the result as an average emitting power LDP. In other words, the average emitting power LDP is calculated by the following formula; LDP=K1×P1+K2×P2+K3×P3+K4×P4. Here, the factors K1, K2, K3 and K4 are positive real values, and respectively correspond to the rates of the emitting time at the emitting power levels P1, P2, P3 and P4. Even if the input data has little randomness, the recording data to be recorded on the optical disk 101 can be in a state close to random due to ECC (error correcting code) processing or the like. Therefore, the recorded data at least can be regarded as a random signal, thus establishing the adequacy of obtaining the average emitting power. The laser driving section 105 in FIG. 1 drives the laser light source 100 in accordance with the value of the emitting power instruction LD from the power adjusting section 104.

An AS (all-sum) signal detecting section 107 in FIG. 1 receives the sum of the plural detected signals (that is, an all-reflected signal) detected by the photodetector 102, and outputs an AS signal with the magnitude that is proportional to that of the reflected light from the optical disk 101. A BDO (Black Dot) detecting section 108 compares the AS signal from the AS signal detecting section 107 with a comparative value LDC1 that is obtained by multiplying the value of the average emitting power LDP from the power adjusting section 104 by the factor KC1: When the AS signal is larger than the comparative value LDC1, the BDO detecting section 108 outputs a signal of "L" as the hold signal BDO1; when the AS signal is not larger than the comparative value LDC1, the BDO detecting section 108 outputs a signal of "H" as the hold signal BDO1. Here, when the AS signal is equal to the comparative value LDC1, the hold signal BDO1 can be selected from "L" and "H" as appropriate, but generally "H" is selected. The factor KC1 is determined so that the hold signal BDO1 from the BDO detecting section 108 can be "L" when the optical disk 101 has no deficiency thereon. The hold signal BDO1 from the BDO detecting section 108 is input into the hold section 109 of the tracking control section. Here, the BDO detecting section 108 composes the deficiency detecting section, and the comparative value LDC1 indicates the threshold value.

As mentioned above, the tracking control section includes the photodetector 102, the tracking error detecting section 106, the hold section 109, the control processing section 110, the tracking driving section 111 and the tracking actuator 112, and the recording/reproducing apparatus further includes the RF signal detecting section 103, the power adjusting section 104, the laser driving section 105, the AS signal detecting section 107 and the BDO detecting section 108 (the deficiency detecting section).

According to the configuration mentioned above, deficiencies on the optical disk 101 can be detected accurately, even when the emitting power of the laser light source 100 changes. Details are described below.

Figure 3:
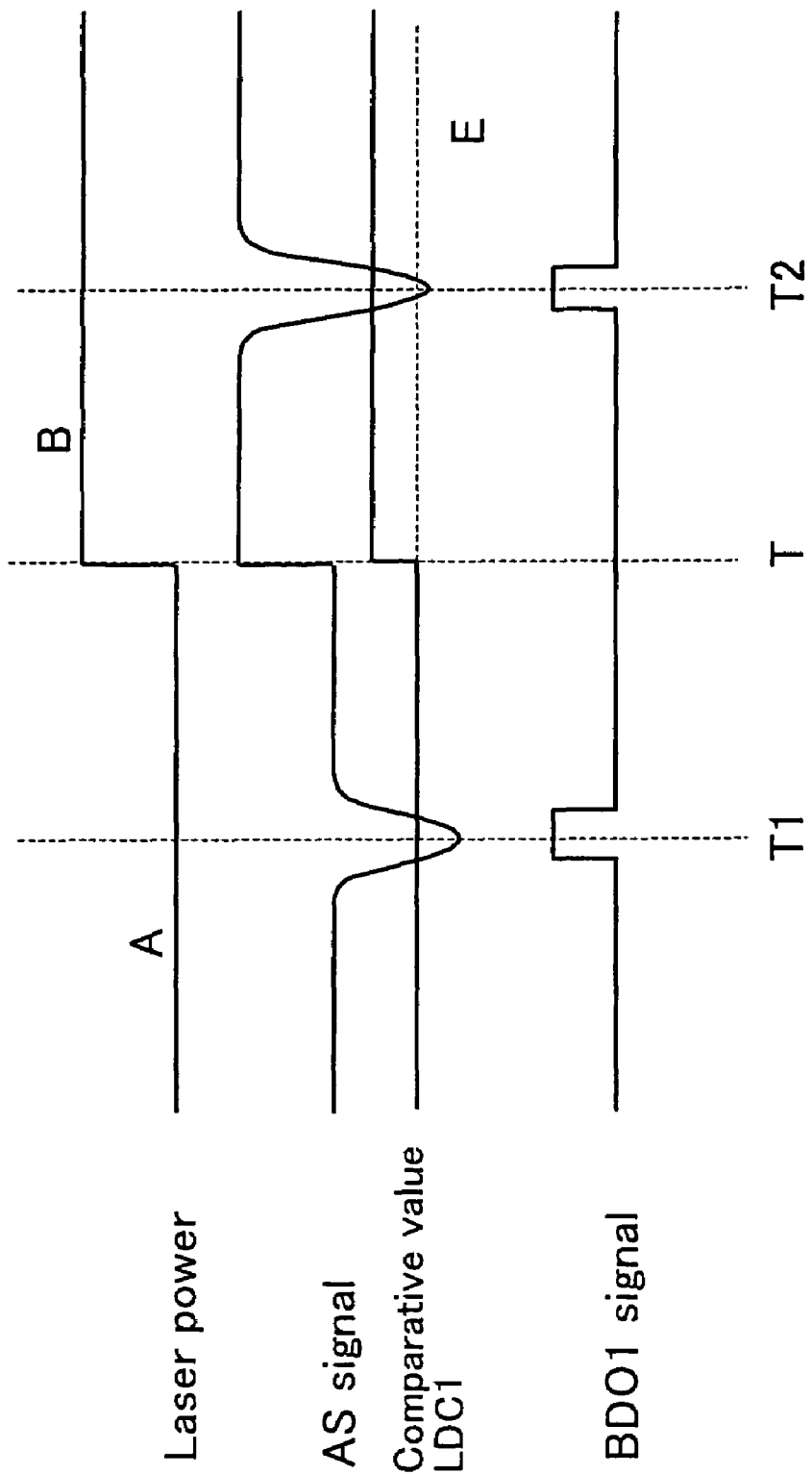
FIG. 3 is a wave form chart of a signal of each part for explaining the operation in Embodiment 1 of the present invention.

FIG. 3 is a wave form chart of an AS signal, a comparative value LDC1 and a hold signal BDO1 when the emitting power of the laser light source 100 changes. In FIG. 3, the horizontal axis indicates time. In FIG. 3, a signal corresponding to the average value of the emitting power is shown as a laser power, which changes from a level A to a level B at a timing T. When the emitting power of the laser light source 100 changes, the AS signal from the AS signal detecting section 107 changes in accordance with the amount of the reflected light from the optical disk 101. Thus the AS signal also changes in accordance with the change of the laser power.

FIG. 3 shows a state wherein deficiencies lie on the optical disk 101 at the timing T1 at the level A with a low laser power and at the timing T2 at the level B with a high laser power. First, when a deficiency lies on the optical disk 101 at the timing T1, the amount of the reflected light from the optical disk 101 decreases. Accordingly, the signal value of the AS signal from the AS signal detecting section 107, which changes in accordance with the amount of the reflected light, decreases. When the value of the AS signal decreases below the comparative value LDC1 of the BDO detecting section 108, the hold signal BDO1 is output. Here, the accuracy of the deficiency detection on the optical disk 101 before changing the emitting power of the laser light source 100 is the same as that in a conventional one.

Next, the operation when a deficiency lies on the optical disk 101 at the timing T2 will be described. After the timing T, the laser power has changed from the level A to the level B, therefore, the value of the AS signal from the AS signal detecting section 107 also changes in accordance with the change of the laser power. If the deficiency lies on the optical disk 101 during this time, the amount of the reflected light from the optical disk 101 decreases, thus the signal value of the AS signal from the AS signal detecting section 107, which changes in accordance with the amount of the reflected light, also is reduced. However, since the comparative value LDC1 of the BDO detecting section 108 is set to be a value that is proportional to the emitting power of the laser light source, the comparative value LDC1 changes in accordance with the emitting power at the timing T as shown in FIG. 3. Thereby, by comparing the value of the AS signal with the comparative value LDC1 by the BDO detecting section 108, the hold signal BDO1 can be generated. Here, in the case of the configuration where the comparative value LDC1 of the BDO detecting section 108 is not changed in accordance with the amount of the emitting power of the laser light source 100 (this case is illustrated by the broken line E of the comparative value LDC1 in FIG. 3), the accuracy of the deficiency detection on the optical disk 101 deteriorates remarkably.

As mentioned above, the deficiency detecting apparatus of the present embodiment can detect a deficiency on the optical disk 101 with high accuracy, even when the emitting power of the laser light source 100 changes.

Moreover, in the present embodiment, the hold signal BDO1 from the BDO detecting section 108 allows the servo tracking signal STE to be held to zero at the hold section 109 of the tracking control section. Thereby, the deficiency detecting apparatus of the present embodiment can realize a stable tracking control, even when the emitting power of the laser light source 100 changes and the optical disk 101 has a deficiency thereon.

Here, in the present embodiment, the comparative value LDC1 of the BDO detecting section 108 is the value obtained by multiplying the average emitting power LDP by the factor KC1, but the comparative value LDC1 may be obtained by referring to a table value in accordance with the value of the average emitting power LDP. Such a modification also is included in the present invention.

Additionally, in the present embodiment, when calculating the average emitting power of the power adjusting section 104, the factors K1, K2, K3 and K4 are assumed to be the values corresponding respectively to the rate of the emitting time at the emitting power levels P1, P2, P3 and P4. However, the factors may be other ones, as long as they can provide a calculation to obtain an amount in accordance with the average emitting power. Such a modification also is embraced in the present invention.

Embodiment 2

Figure 4:
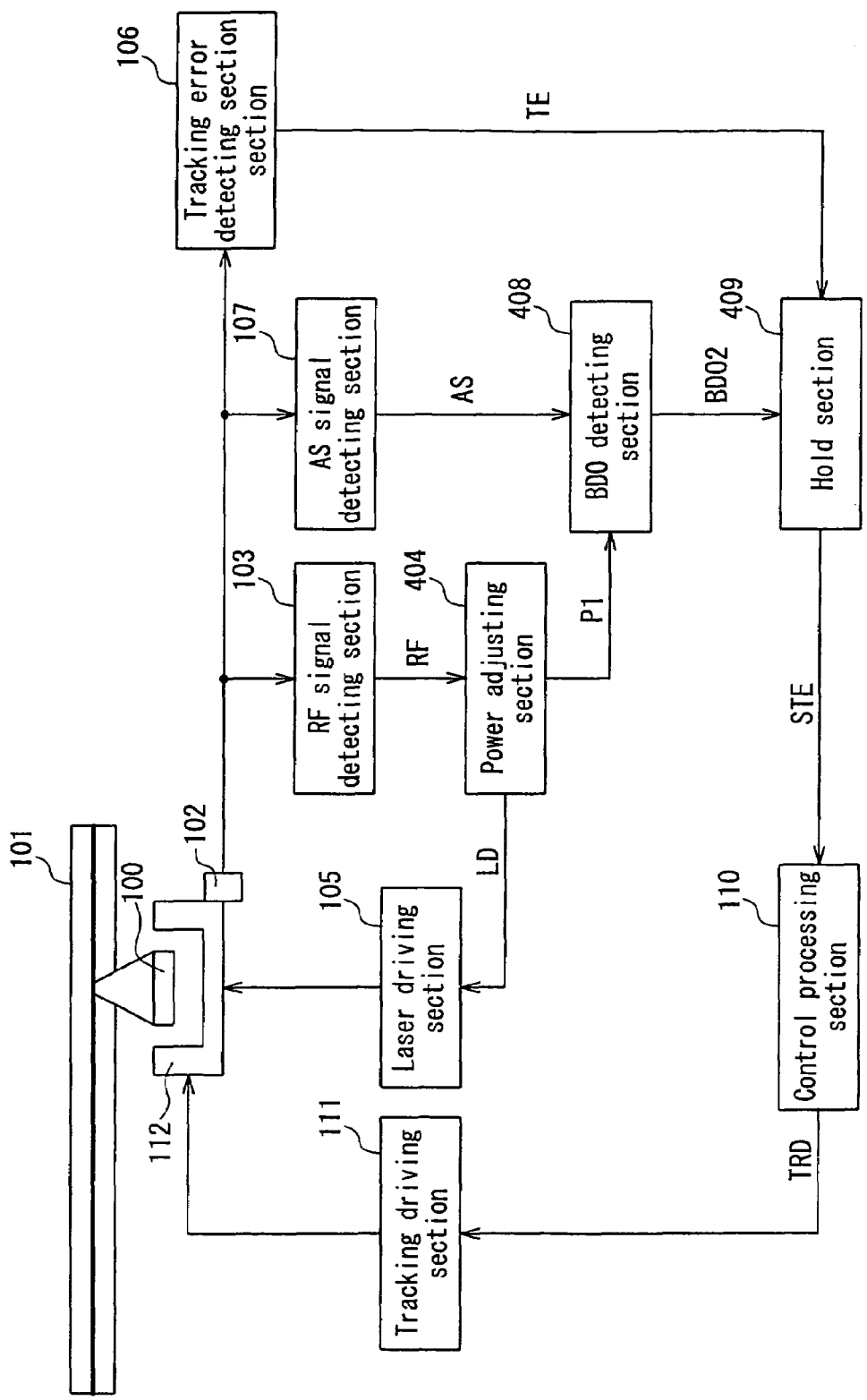
FIG. 4 is a block diagram showing an example of the configuration of the deficiency detecting apparatus according to Embodiment 2 of the present invention.

FIG. 4 is a block diagram showing an example of the configuration of a deficiency detecting apparatus according to Embodiment 2 of the present invention. In FIG. 4, a photodetector 102, a tracking error detecting section 106, a control processing section 110, a tracking driving section 111, a tracking actuator 112, a RF signal detecting section 103, a laser driving section 105 and an AS signal detecting section 107 are the same as those in Embodiment 1. Thus the explanation thereof will be omitted.

A hold section 409 of the deficiency detecting apparatus according to the present embodiment shown in FIG. 4 receives a tracking error signal TE from the tracking error detecting section 106 and a below-described hold signal BDO2, performs hold processing to the tracking error signal TE in accordance with the hold signal BDO2, and subsequently outputs a servo tracking error signal STE. More specifically, the hold section 409 outputs the tracking error signal TE as the servo tracking error signal STE when the hold signal BDO2 is "L", and outputs a zero signal as the servo tracking error signal STE when the hold signal BDO2 is "H".

Similarly to Embodiment 1, a power adjusting section 404 of the deficiency detecting apparatus of the present embodiment receives a reproducing signal RF from the RF signal detecting section 103, and outputs an emitting power instruction LD for the laser light source 100 so that the reproducing signal RF can be optimum.

Moreover, the power adjusting section 404 in FIG. 4 outputs an emitting power level P1 that is the highest power level among four emitting power levels P1, P2, P3 and P4 of the emitting power instruction LD.

A BDO detecting section 408 compares an AS signal from the AS signal detecting section 107 with a comparative value LDC2 that is obtained by multiplying the value of the emitting power level P1 from the power adjusting section 404 by a factor KC2: When the AS signal is larger than the comparative value LDC2, the BDO detecting section 408 outputs a signal of "L" as the hold signal BDO2; when the AS signal is not larger than the comparative value LDC2, the BDO detecting section 408 outputs a signal of "H" as the hold signal BDO2. Here, when the AS signal is equal to the comparative value LDC2, the hold signal BDO2 can be selected from "L" and "H" as appropriate, but generally "H" is selected. The factor KC2 is determined so that the hold signal BDO2 from the BDO detecting section 408 can be "L" when the optical disk 101 has no deficiency or the like thereon. The hold signal BDO2 from the BDO detecting section 408 is input into the hold section 409 of the tracking control section. Here, the BDO detecting section 408 composes the deficiency detecting section.

According to the configuration mentioned above, in the present embodiment as well as Embodiment 1, deficiencies on the optical disk 101 can be detected accurately even when the emitting power of the laser light source 100 changes.

Furthermore, similarly to Embodiment 1, a stable tracking control can be realized even when the emitting power of the laser light source 100 changes and the optical disk 101 has a deficiency thereon.

Still further, in the present embodiment, the operation of the BDO detecting section 408 allows the comparison of the AS signal from the AS signal detecting section 107 with the comparative value LDC2 that is obtained by multiplying the value of the emitting power level P1 from the power adjusting section 404 by the factor KC2, thereby generating the hold signal BDO2. Accordingly, the configuration of the power adjusting section can be simplified more than that of Embodiment 1. That is, the emitting power instruction LD for the laser light source 100 consists of the plural emitting power levels P1, P2, P3 and P4, and the magnitude of the emitting power instruction is mostly determined by the emitting power level P1 that is the highest value of the emitting power. As a result, the process to obtain the average emitting power LDP, which is in the configuration of Embodiment 1, can be omitted, thereby enabling the configuration of the power adjusting section to be simplified.

Embodiment 3

Figure 5:
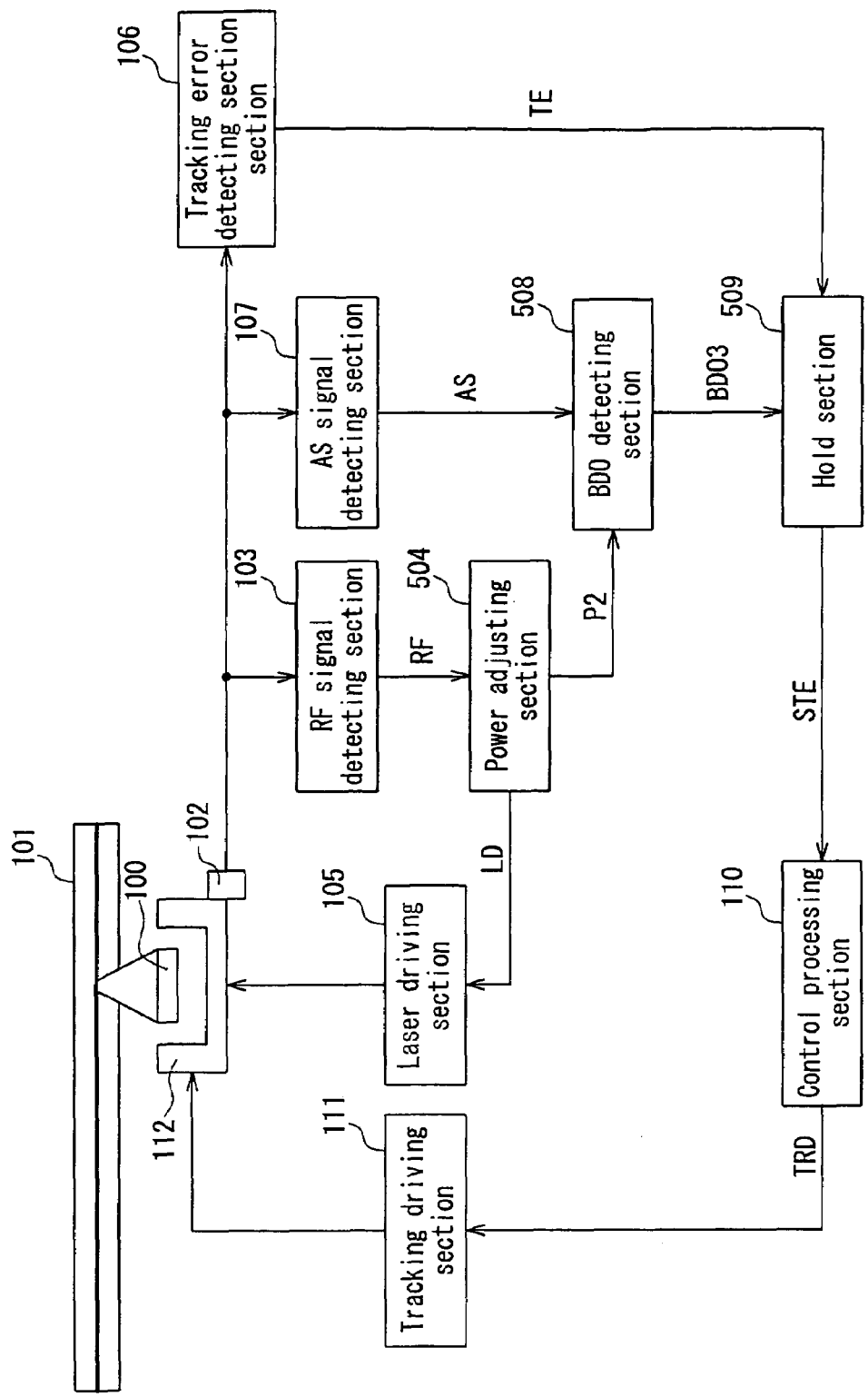
FIG. 5 is a block diagram showing an example of configuration of the deficiency detecting apparatus according to Embodiment 3 of the present invention.

FIG. 5 is a block diagram showing an example of the configuration of a deficiency detecting apparatus according to Embodiment 3 of the present invention. In FIG. 5, a photodetector 102, a tracking error detecting section 106, a control processing section 110, a tracking driving section 111, a tracking actuator 112, a RF signal detecting section 103, a laser driving section 105 and an AS signal detecting section 107 are the same as those in Embodiment 1. Thus the explanation thereof will be omitted.

A hold section 509 of the present embodiment receives a tracking error signal TE from the tracking error detecting section 106 and a below-described hold signal BDO3, performs hold processing to the tracking error signal TE in accordance with the hold signal BDO3, and subsequently outputs a servo tracking error signal STE. More specifically, the hold section 509 outputs the tracking error signal TE as the servo tracking error signal STE when the hold signal BDO3 is "L", and outputs a zero signal as the servo tracking error signal STE when the hold signal BDO3 is "H".

Similarly to Embodiment 1, a power adjusting section 504 of the present embodiment receives a reproducing signal RF from the RF signal detecting section 103, and outputs an emitting power instruction LD for the laser light source 100 so that the reproducing signal RF can be optimum.

Moreover, the power adjusting section 504 in FIG. 5 outputs an emitting power level P2 that is a power level for erasing among four emitting power levels P1, P2, P3 and P4 of the emitting power instruction LD.

A BDO detecting section 508 compares an AS signal from the AS signal detecting section 107 with a comparative value LDC3 that is obtained by multiplying the value of the emitting power level P2 from the power adjusting section 504 by a factor KC3: When the AS signal is larger than the comparative value LDC3, the BDO detecting section 508 outputs a signal of "L" as the hold signal BDO3; when the AS signal is not larger than the comparative value LDC3, the BDO detecting section 508 outputs a signal of "H" as the hold signal BDO3. Here, when the AS signal is equal to the comparative value LDC3, the hold signal BDO3 can be selected from "L" and "H" as appropriate, but generally "H" is selected. The factor KC3 is determined so that the hold signal BDO3 from the BDO detecting section 508 can be "L" when the optical disk 101 has no deficiency or the like thereon. The hold signal BDO3 from the BDO detecting section 508 is input into the hold section 509 of the tracking control section. Here, the BDO detecting section 508 composes the deficiency detecting section.

According to the configuration mentioned above, even when the emitting power of the laser light source 100 changes, deficiencies on the optical disk 101 can be detected accurately, which is the same as Embodiment 1.

Furthermore, as well as Embodiment 1, a stable tracking control can be realized, even when the emitting power of the laser light source 100 changes and the optical disk 101 has a deficiency thereon.

Still further, in Embodiment 3, the operation of the BDO detecting section 508 allows the comparison of the AS signal from the AS signal detecting section 107 with the comparative value LDC3 that is obtained by multiplying the value of the emitting power level P2 from the power adjusting section 504 by the factor KC3, thereby generating the hold signal BDO3. Accordingly, the configuration of the power adjusting section can be simplified.

That is, the emitting power instruction LD for the laser light source 100 consists of the plural emitting power levels P1, P2, P3 and P4, and the emitting power level P2, which is a power for erasing a signal, is output relatively longer than the other power levels. Accordingly, deficiencies also can be detected in accordance with the emitting power level P2. By using the emitting power level P2 as above, the process for obtaining the average emitting power LDP, which is in the configuration of Embodiment 1, becomes unnecessary, thereby enabling a system to be simplified.

Embodiment 4

Figure 6:
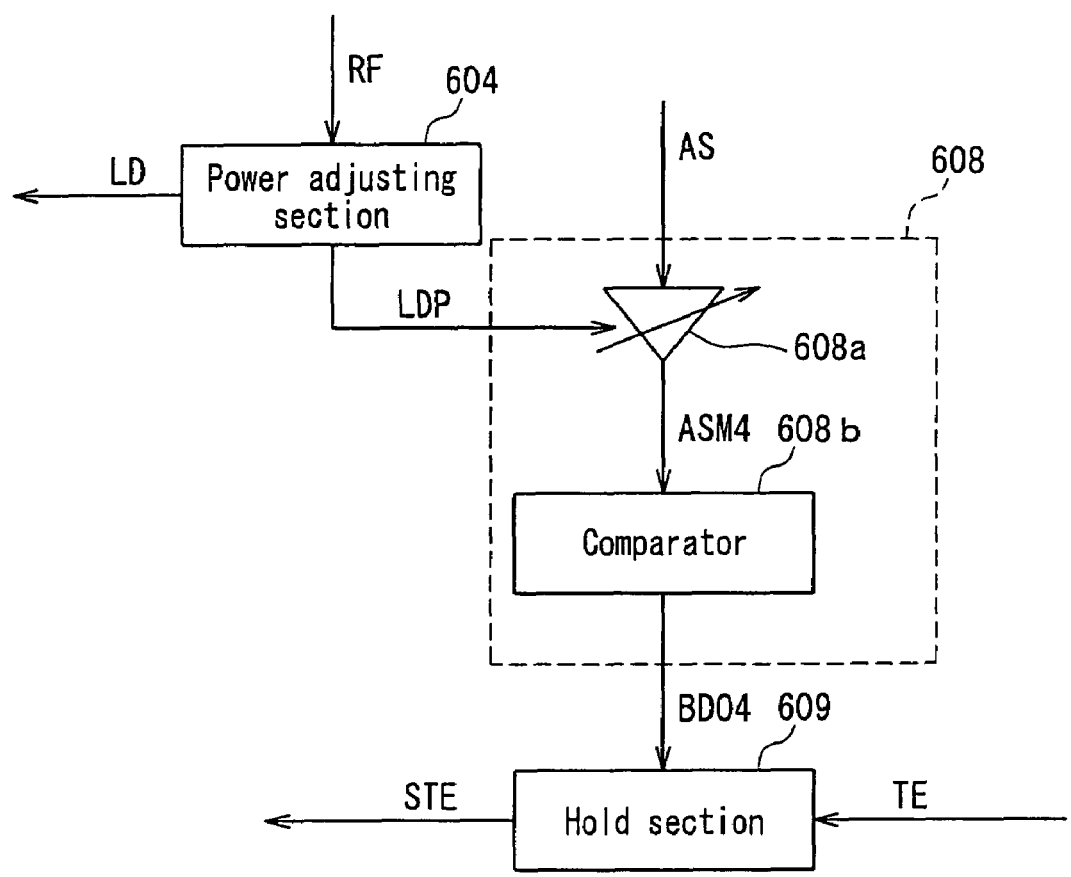
FIG. 6 is a block diagram showing an example of the configuration of a power adjusting section, a BDO detecting section and a hold section in the deficiency detecting apparatus according to Embodiment 4 of the present invention.

FIG. 6 is a block diagram showing the main configuration of a deficiency detecting apparatus according to Embodiment 4 of the present invention. A photodetector 102, a tracking error detecting section 106, a control processing section 110, a tracking driving section 111, a tracking actuator 112, a RF signal detecting section 103, a laser driving section 105 and an AS signal detecting section 107, which are not shown in FIG. 6, are the same as those in Embodiment 1. Thus the explanation thereof will be omitted. A hold section 609, a power adjusting section 604 and a BDO detecting section 608 in FIG. 6 are different from those in Embodiment 1.

The hold section 609 of the present embodiment receives a tracking error signal TE from the tracking error detecting section 106 and a below-described hold signal BDO4, performs hold processing to the tracking error signal TE in accordance with the hold signal BDO4, and subsequently outputs a servo tracking error signal STE. More specifically, the hold section 609 outputs the tracking error signal TE as the servo tracking error signal STE when the hold signal BDO4 is "L", and outputs a zero signal as the servo tracking error signal STE when the hold signal BDO4 is "H".

The power adjusting section 604 of the present embodiment has the same configuration as the power adjusting section 104 of Embodiment 1. That is, similarly to Embodiment 1, the power adjusting section 604 receives a reproducing signal RF from the RF signal detecting section 103, and outputs an emitting power instruction LD for the laser light source 100 so that the reproducing signal RF can be optimum. Thereafter, the power adjusting section 604 obtains an average value of the emitting power instruction LD by the weighted summation of the four emitting powers, and outputs the result as an average emitting power LDP. The average emitting power LDP is obtained by the following calculation; $LDP = K1 \times P1 + K2 \times P2 + K3 \times P3 + K4 \times P4$. Here, the factors K1, K2, K3 and K4 are positive real values, and respectively correspond to the rates of the emission time of the emitting power levels P1, P2, P3 and P4.

The BDO detecting section 608 in FIG. 6 is composed of an amplifier 608a and a comparator 608b. The AS signal from the AS signal detecting section 107 and the average emitting power LDP from the power adjusting section 604 are input into the amplifier 608a, and the AS signal is amplified at an amplification rate that is controlled by the average emitting power (in the present embodiment, the amplification factor is controlled to decrease as the average emitting power LDP increases), and is output as an ASM signal (ASM4). That is, the ASM4 corresponds to the signal for amplified reflected light amount.

The ASM4 is input into the comparator 608b of the BDO detecting section 608, and is compared with a predetermined threshold value R: When the ASM4 is larger than the predetermined threshold value R, the comparator 608b outputs a signal of "L" as the hold signal BDO4; when the ASM4 is not larger than the predetermined threshold value R, the comparator 608b outputs a signal of "H" as the hold signal BDO4. Here, when the ASM signal is equal to the predetermined threshold value R, the hold signal BDO4 can be selected from "L" and "H" as appropriate, but generally "H" is selected. The predetermined threshold value R is determined so that the hold signal BDO4 from the BDO detecting section 608 can be "L" when the optical disk 101 has no deficiency or the like thereon. The hold signal BDO4 from the BDO detecting section 608 is input into the hold section 609 of the tracking control section. Here, the BDO detecting section 608 composes the deficiency detecting section.

According to the configuration mentioned above, even when the emitting power of the laser light source 100 changes, deficiencies on the optical disk 101 can be detected accurately. This will be described in detail below, with reference to FIG. 7.

Figure 7:
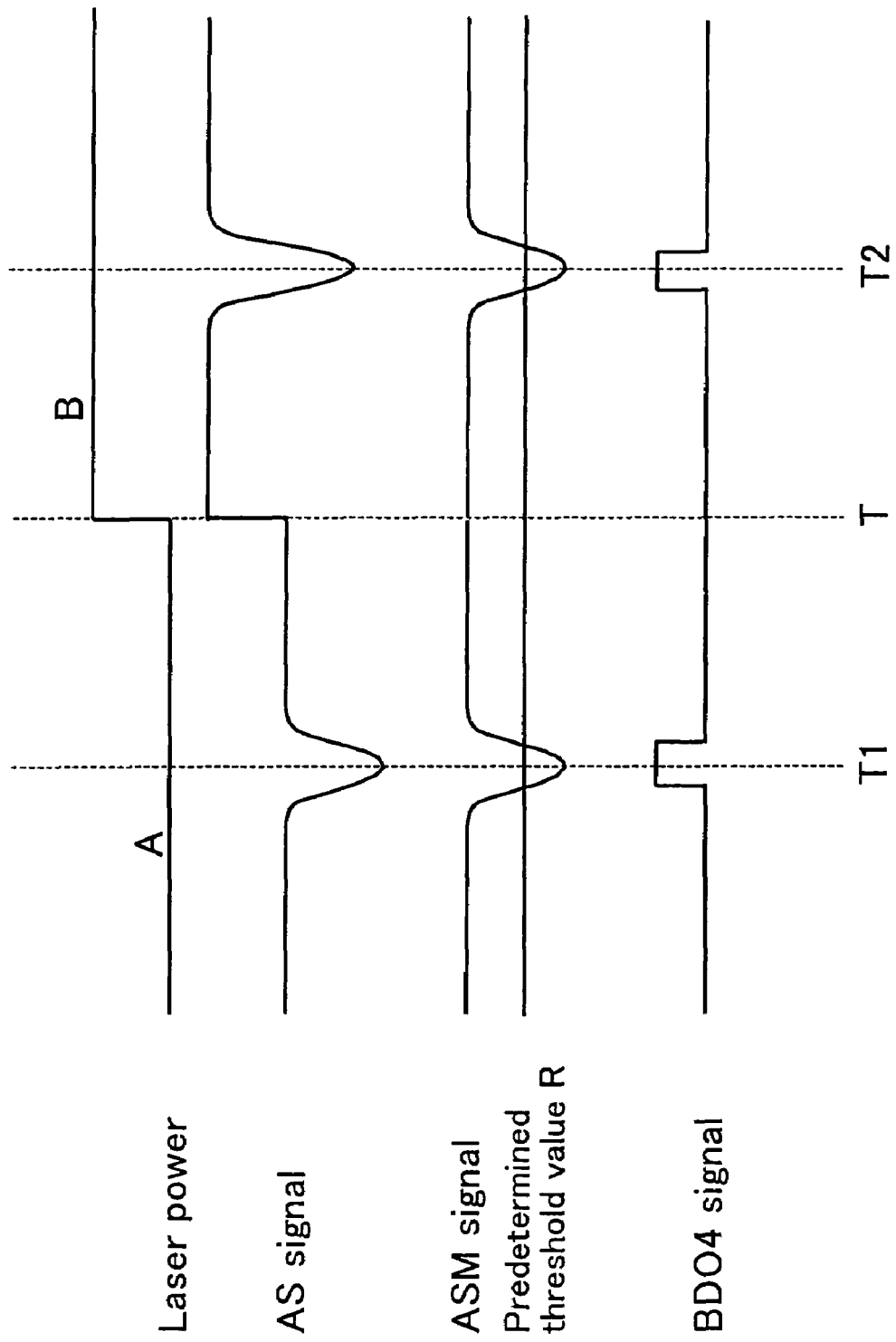
FIG. 7 is a wave form chart of a signal of each part for explaining the operation of the power adjusting section and the BDO detecting section and the hold section in Embodiment 4 of the present invention.

FIG. 7 is a wave form chart of the AS signal, the ASM signal, the predetermined threshold value R and the hold signal BDO4 when the emitting power of the laser light source 100 changes. In FIG. 7, the horizontal axis indicates time. In FIG. 7, a signal corresponding to the average value of the emitting power is shown as a laser power, which changes from a level A to a level B at a timing T. When the emitting power of the laser light source 100 changes, the AS signal from the AS signal detecting section 107 changes in accordance with the amount of the reflected light from the optical disk 101. Thus the AS signal also changes in accordance with the change of the laser power.

However, the ASM signal (ASM4) from the amplifier 608a of the BDO detecting section 608 is a signal that is obtained by amplifying the AS signal at an amplification factor in accordance with the average emitting power LDP from the power adjusting section 604. Thus the level change at the timing T does not occur substantially. That is, the change in the laser power at the timing T is almost equivalent to the change in the average emitting power LDP. In addition, since the amplifier 608a of the BDO detecting section 608 is configured to provide a lower amplification factor as the average emitting power LDP increases, the AS signal level that has been raised in accordance with the increment of the laser power decreases, and the ASM signal that is an output signal of the amplifier 608a is hardly affected by the increment of the laser power. Thereby, the level of the ASM signal does not change substantially at the timing T.

Referring to FIG. 7, the operation when a deficiency lies on the optical disk 101 at the timing T2 is described. After the timing T, the laser power has changed from the level A to the level B, accordingly, the value of the AS signal from the AS signal detecting section 107 changes in accordance with the change of the laser power. However, the ASM signal does not change substantially due to the operation of the amplifier 608a. Therefore, deficiencies on the optical disk 101 can be detected with an excellent accuracy, only by comparing the ASM signal with the predetermined threshold value R using the comparator 608b of the BDO detecting section 608.

According to the configuration mentioned above, even when the emitting power of the laser light source 100 of the present embodiment changes, deficiencies on the optical disk 101 can be detected accurately, which is the same as Embodiment 1. Furthermore, as well as Embodiment 1, a stable tracking control can be realized even when the emitting power of the laser light source 100 changes and the optical disk 101 has a deficiency thereon.

Still further, in the present embodiment, the operation of the amplifier 608a of the BDO detecting section 608 allows the removal of a level fluctuation caused by the laser power change from the AS signal to generate the ASM signal, and then the comparison by the comparator 608b of the ASM signal with the predetermined threshold value R enables the detection of the hold signal BDO4. According to the above configuration, the saturation of an input signal of the comparator 608b generated when the laser power is high and the degradation of a noise margin of an input signal of the comparator 608b generated when the laser power is low can be prevented. Thus the hold signal BDO4 with an excellent reliability can be detected.

The present embodiment has the configuration where the amplification factor of the amplifier 608a of the BDO detecting section 608 decreases, with increases in the average emitting power LDP. However, the amplification factor is not limited to the above operation, and can change discretely in accordance with the average emitting power LDP. Such a modification also is embraced in the present invention.

Embodiment 5

Figure 8:
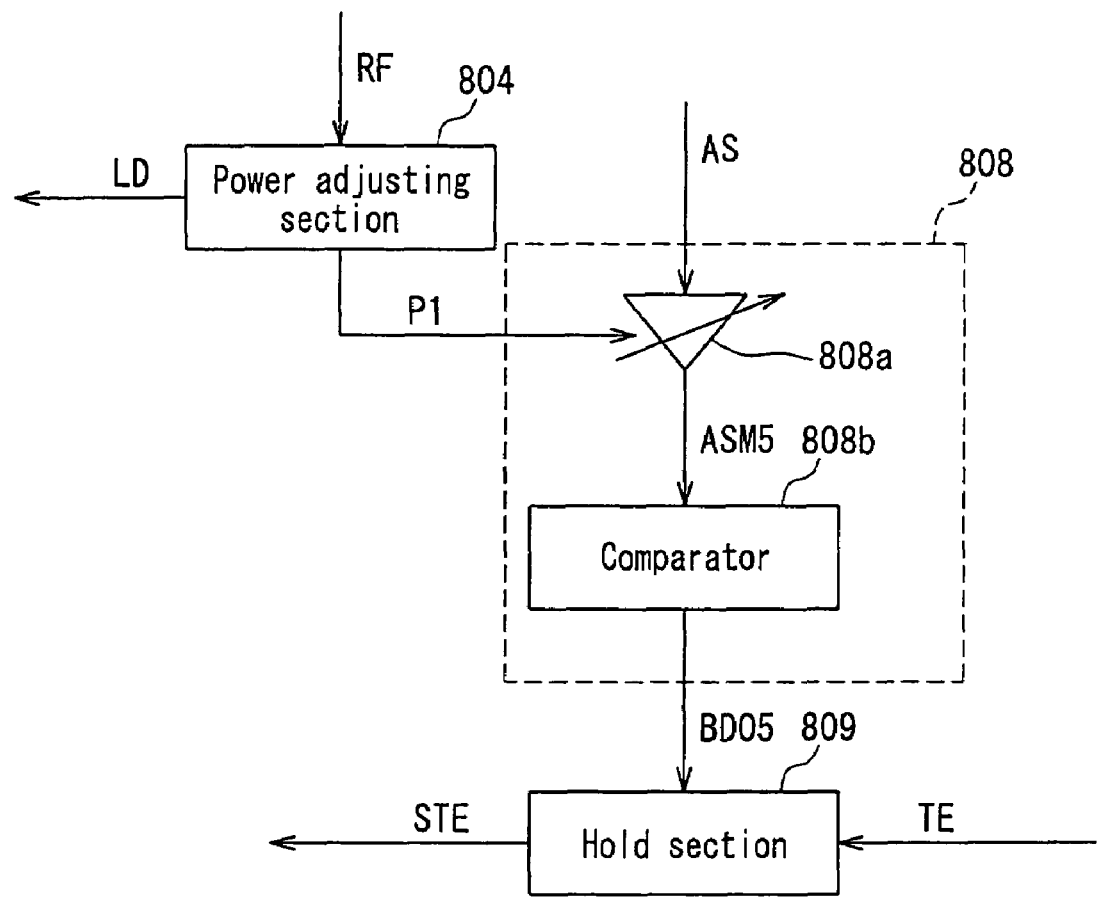
FIG. 8 is a block diagram showing an example of the configuration of a power adjusting section, a BDO detecting section and a hold section in the deficiency detecting apparatus according to Embodiment 5 of the present invention.

FIG. 8 is a block diagram showing the main configuration of a deficiency detecting apparatus according to Embodiment 5 of the present invention. A photodetector 102, a tracking error detecting section 106, a control processing section 110, a tracking driving section 111, a tracking actuator 112, a RF signal detecting section 103, a laser driving section 105 and an AS signal detecting section 107, which are not shown in FIG. 8, are the same as those in Embodiment 1. Thus the explanation thereof will be omitted. A hold section 809, a power adjusting section 804 and a BDO detecting section 808 in FIG. 8, which are different from those in Embodiment 1, will be described below.

The hold section 809 of the present embodiment receives a tracking error signal TE from the tracking error detecting section 106 and a below-described hold signal BDO5, performs hold processing to the tracking error signal TE in accordance with the hold signal BDO5, and subsequently outputs a servo tracking error signal STE. More specifically, the hold section 809 outputs the tracking error signal TE as the servo tracking error signal STE when the hold signal BDO5 is "L", and outputs a zero signal as the servo tracking error signal STE when the hold signal BDO5 is "H".

Similarly to Embodiment 2, the power adjusting section 804 of the present embodiment receives a reproducing signal RF from the RF signal detecting section 103, and outputs an emitting power instruction LD for the laser light source 100 so that the reproducing signal RF can be optimum. Moreover, the power adjusting section 804 outputs an emitting power level P1 that is the highest power level among four emitting power levels P1, P2, P3 and P4 of the emitting power instruction LD.

The BDO detecting section 808 of the present embodiment is composed of an amplifier 808a and a comparator 808b. The AS signal from the AS signal detecting section 107 and the emitting power level P1 from the power adjusting section 804 are input into the amplifier 808a, and the AS signal is amplified at an amplification factor that is controlled by the emitting power level P1(in the present embodiment, the amplification factor is controlled to decrease as the emitting power level P1 increases), and is output as an ASM signal (ASM5). That is, the ASM5 corresponds to the signal for amplified reflected light amount.

The ASM5 is input into the comparator 808b of the BDO detecting section 808, where the ASM5 is compared with a predetermined threshold value R: When the ASM5 is larger than the predetermined threshold value R, the comparator 808b outputs a signal of "L" as the hold signal BDO5; when the ASM5 is not larger than the predetermined threshold value R, the comparator 808b outputs a signal of "H" as the hold signal BDO5. Here, when the ASM signal is equal to the predetermined threshold value R, the hold signal BDO5 can be selected from "L" and "H" as appropriate, but generally "H" is selected. The predetermined threshold value R is determined so that the hold signal BDO5 from the BDO detecting section 808 can be "L" when the optical disk 101 has no deficiency or the like thereon. The hold signal BDO5 from the BDO detecting section 808 is input into the hold section 809 of the tracking control section. Here, the BDO detecting section 808 composes the deficiency detecting section.

According to the configuration mentioned above, also in the present embodiment, even when the emitting power of the laser light source 100 changes, deficiencies on the optical disk 101 can be detected accurately, which is the same as Embodiment 1. Furthermore, as well as Embodiment 1, stable tracking control can be realized even when the emitting power of the laser light source 100 changes and the optical disk 101 has a deficiency thereon.

Moreover, in the present embodiment, by the operation of the BDO detecting section 808 allows the utilization of the AS signal from the AS signal detecting section 107 and the emitting power level P1 from the power adjusting section 804, and the operation of the amplifier 808a of the BDO detecting section 808 allows the removal of a level fluctuation caused by the laser power change from the AS signal to generate the ASM5. Further, by comparing the ASM5 with the predetermined threshold value R using the comparator 608b, the hold signal BDO5 is detected. According to the configuration mentioned above, the saturation of an input signal of the comparator 608b generated when the laser power is high and the degradation of a noise margin of an input signal of the comparator 608b generated when the laser power is low can be prevented, and the hold signal BDO5 with an excellent reliability can be detected. Additionally, the configuration of the power adjusting section can be simplified more than that in Embodiment 1. Therefore, the configuration can satisfy both of the simplified power adjusting section and the BDO detecting section with a high precision.

Embodiment 6

Figure 9:
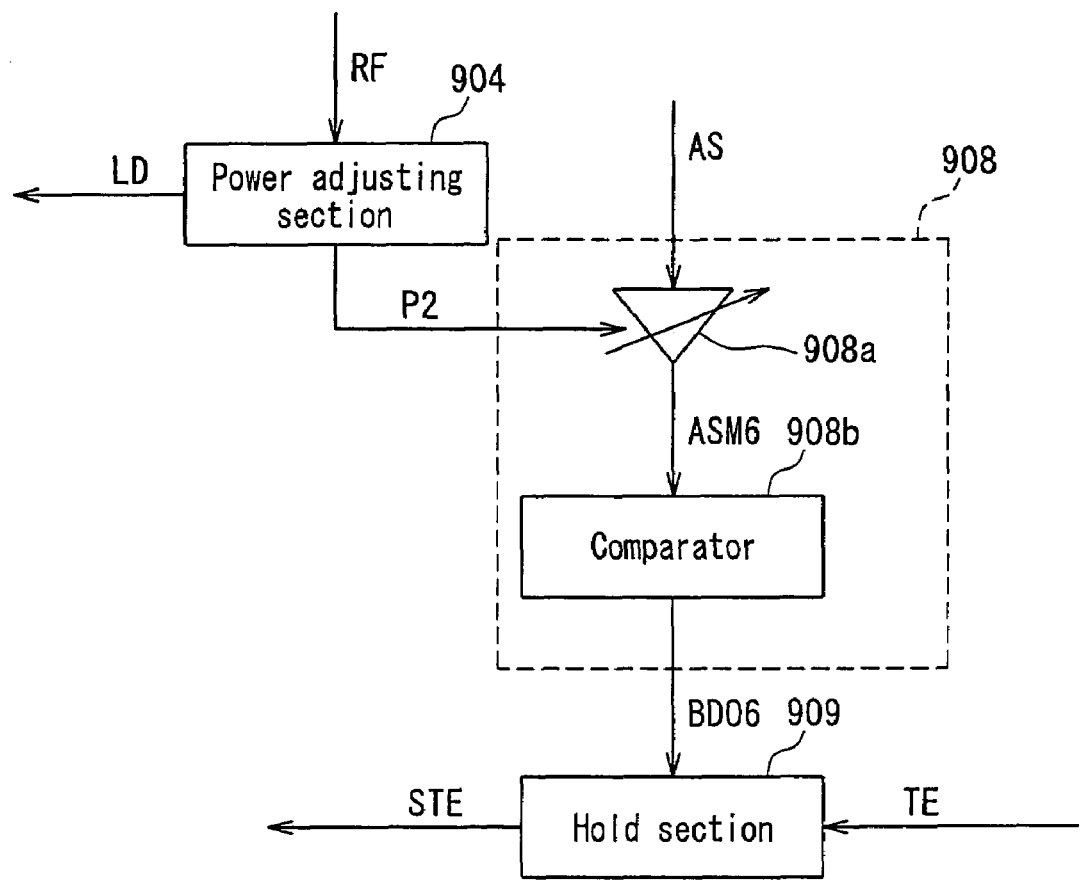
FIG. 9 is a block diagram showing an example of the configuration of a power adjusting section, a BDO detecting section and a hold section in the deficiency detecting apparatus according to Embodiment 6 of the present invention.

FIG. 9 is a block diagram showing the main configuration of a deficiency detecting apparatus according to Embodiment 6 of the present invention. A photodetector 102, a tracking error detecting section 106, a control processing section 110, a tracking driving section 111, a tracking actuator 112, a RF signal detecting section 103, a laser driving section 105 and an AS signal detecting section 107, which are not shown in FIG. 9, are the same as those in Embodiment 1. Thus the explanation thereof will be omitted. A hold section 909, a power adjusting section 904 and a BDO detecting section 908, which are different from those in Embodiment 1, will be described below.

The hold section 909 of the present embodiment receives a tracking error signal TE from the tracking error detecting section 106 and a below-described hold signal BDO6, performs hold processing to the tracking error signal TE in accordance with the hold signal BDO6, and subsequently outputs a servo tracking error signal STE. More specifically, the hold section 909 outputs the tracking error signal TE as the servo tracking error signal STE when the hold signal BDO6 is "L", and outputs a zero signal as the servo tracking error signal STE when the hold signal BDO6 is "H".

Similarly to Embodiment 3, the power adjusting section 904 of the present embodiment receives a reproducing signal RF from the RF signal detecting section 103, and outputs an emitting power instruction LD for the laser light source 100 so that the reproducing signal RF can be optimum.

Moreover, the power adjusting section 904 outputs an emitting power level P2 that is a power level for erasing among four emitting power levels P1, P2, P3 and P4 of the emitting power instruction LD.

The BDO detecting section 908 of the present embodiment is composed of an amplifier 908a and a comparator 908b. The AS signal from the AS signal detecting section 107 and the emitting power level P2 from the power adjusting section 904 are input into the amplifier 908a, and the AS signal is amplified at an amplification factor that is controlled by the emitting power level P2 (in the present embodiment, the amplification factor is controlled to decrease as the emitting power level P2 increases), and is output as an ASM signal (ASM6). That is, the ASM6 corresponds to the signal for amplified reflected light amount.

The ASM6 is input into the comparator 908b of the BDO detecting section 908, where the ASM6 is compared with a predetermined threshold value R: When the ASM6 is larger than the predetermined threshold value R, the comparator 908b outputs a signal of "L" as the hold signal BDO6; when the ASM6 is not larger than the predetermined threshold value R, the comparator 908b outputs a signal of "H" as the hold signal BDO6. Here, when the ASM signal is equal to the predetermined threshold value, the hold signal BDO6 can be selected from "L" and "H" as appropriate, but generally "H" is selected. The predetermined threshold value R is determined so that the hold signal BDO6 from the BDO detecting section 908 can be "L" when the optical disk 101 has no deficiency or the like thereon. The hold signal BDO6 from the BDO detecting section 908 is input into the hold section 909 of the tracking control section. Here, the BDO detecting section 908 composes the deficiency detecting section.

According to the configuration mentioned above, also in the present embodiment, even when the emitting power of the laser light source 100 changes, deficiencies on the optical disk 101 can be detected accurately, which is the same as Embodiment 1. Furthermore, as well as Embodiment 1, a stable tracking control can be realized even when the emitting power of the laser light source 100 changes and the optical disk 101 has a deficiency thereon.

Moreover, in the present embodiment, the operation of the BDO detecting section 908 allows the utilization of the AS signal from the AS signal detecting section 107 and the emitting power level P2 from the power adjusting section 904, and the operation of the amplifier 908a of the BDO detecting section 908 allows the removal of a level fluctuation caused by the laser power change from the AS signal to generate the ASM signal. Further, by comparing the ASM signal with the predetermined threshold value R using the comparator 908b, the hold signal BDO6 is detected. According to the above configuration, the saturation of an input signal of the comparator 908b generated when the laser power is high and degradation of a noise margin of an input signal of the comparator 908b generated when the laser power is low can be prevented, thus the hold signal BDO6 can be detected with excellent reliability. Additionally, the configuration of the power adjusting section can be simplified more than that of Embodiment 1. Thus, the configuration can satisfy both of the simplified power adjusting section and the BDO detecting section with a high precision.

In Embodiments 1 to 6, the BDO detecting section and the power adjusting section are individual functional parts, however, the output signal from the photodetector may be converted into a digital signal and a process equivalent those performed by the BDO detecting section and the power adjusting section may be performed by an arithmetic device such as a microprocessor. Such a modification also is embraced in the present invention.

In addition, in Embodiments 1 to 6, the output power of the emitting power instruction for the laser light source from the power adjusting section is not limited to the pattern shown in FIG. 2, and it is easy to modify this pattern into a pattern having a larger number of levels, a pattern having a smaller number of levels, or a pattern changing continuously. Such modifications also are embraced in the present invention.

Moreover, in Embodiments 1 to 6, deficiencies on the optical disk are detected by the BDO detecting section, but an object to be detected by the BDO detecting section is not limited to this. Using the optical disk apparatuses of Embodiments 1 to 6, information can be reproduced from the optical disk, on which the information is recorded by processing the reflective surface of the optical disk so as to change the reflection coefficient thereon. Needless to say, such an application also is embraced in the present invention.

Furthermore, by reproducing the information using the method in Embodiments 1 to 6 from the optical disk, on which the information is recorded by processing the reflective surface so as to change the reflection coefficient thereon, a preliminary check for the operation of the deficiency detection can be performed. By determining various factors and constants for the power adjusting section and the BDO detecting section in accordance with the result of this preliminary check for the operation, reliability for detecting the deficiencies on the optical disk improves dramatically. It is needless to say that such modifications also are embraced in the present invention.

Still further, in Embodiments 1 to 6, the tracking error detecting section, the hold section, the control processing section, the RF signal detecting section, the power adjusting section, the AS signal detecting section and the BDO detecting section are configured separately, but a function equivalent to these parts is possible to be performed by a microprocessor, a sequencer or the like, and at least two blocks can be integrated in one semiconductor circuit. It is needless to say that such modifications are embraced in the present invention.

As described above, according to the deficiency detecting apparatus of the present invention, the operation of the power adjusting section and the BDO detecting section allows the detection of deficiencies on the optical disk accurately, even when the emitting power of the laser light source changes. In particular, according to the configuration of the present invention, the deficiency detecting operation is changed in accordance with the power instruction for the laser, thus deficiencies or the like can be detected with an excellent accuracy responding to the abrupt change of the laser power. If using the result of the deficiency detection on the optical disk, an operation such as stopping the control action of a focus and a tracking control can be carried out. Thereby the operating stability of the optical disk apparatus is improved dramatically.

The invention claimed is:

1. A deficiency detecting apparatus, which detects deficiencies on an information medium that are unable to be recorded or reproduced when an information signal is recorded/reproduced with respect to the information medium using a light beam generated by a laser light source, comprising:
   a power adjusting section for adjusting an emitting power of the laser light source to an optimum value; and
   a deficiency detecting section for comparing a threshold value determined by calculating a non-fixed variable value that varies depending on the emitting power of the laser light source adjusted by the power adjusting section with a value corresponding to reflected light that is the light beam reflected by an information layer of the information medium, and detecting the deficiencies on the information layer in accordance with a result of the comparison.

2. The deficiency detecting apparatus according to claim 1, wherein the deficiency detecting section determines the threshold value in accordance with an emitting power-selected from a predetermined range of laser power.

3. The deficiency detecting apparatus according to claim 1, wherein the deficiency detecting section determines the threshold value in accordance with an average value of the emitting power adjusted by the power adjusting section.

4. The deficiency detecting apparatus according to claim 1, wherein the emitting power adjusted by the power adjusting section is composed of plural power levels, and the deficiency detecting section determines the threshold value in accordance with a value obtained by summing the plural power levels at predetermined rates.

5. The deficiency detecting apparatus according to claim 1, wherein the emitting power adjusted by the power adjusting section is composed of plural power levels, and the deficiency detecting section determines the threshold value in accordance with the highest power level among the plural power levels.

6. The deficiency detecting apparatus according to claim 1, wherein the emitting power adjusted by the power adjusting section is composed of plural power levels, and the deficiency detecting section determines the threshold value in accordance with an erasing power level that is used for erasing among the plural power levels.

7. A deficiency detecting apparatus, which detects deficiencies on an information medium that are unable to be recorded or reproduced when an information signal is recorded/reproduced wit respect to the information medium using a light beam generated by a laser light source, comprising:
   a power adjusting section for adjusting an emitting power of the laser light source to an optimum value; and
   a deficiency detecting section for amplifying a signal corresponding to reflected light that is the light beam reflected by an information layer of the information medium at an amplification factor determined by calculating a non-fixed variable value that varies depending on the emitting power of the laser light source adjusted by the power adjusting section so as to generate a signal for amplified reflected light amount, and for comparing a value corresponding to the signal for the amplified reflected light amount with a predetermined threshold value and detecting the deficiencies on the information layer in accordance with a result of the comparison.

8. The deficiency detecting apparatus according to claim 7, wherein the deficiency detecting section determines the amplification factor in accordance with an emitting power selected from a predetermined range of laser power.

9. The deficiency detecting apparatus according to claim 7, wherein the deficiency detecting section determines the amplification factor in accordance with an average value of the emitting power adjusted by the power adjusting section.

10. The deficiency detecting apparatus according to claim 7, wherein the emitting power adjusted by the power adjusting section is composed of plural power levels, and the deficiency detecting section determines the amplification factor in accordance with a value obtained by summing the plural power levels at predetermined rates.

11. The deficiency detecting apparatus according to claim 7, wherein the emitting power adjusted by the power adjusting section is composed of plural power levels, and the deficiency detecting section determines the amplification factor in accordance with the highest power level among the plural power levels.

12. The deficiency detecting apparatus according to claim 7, wherein the emitting power adjusted by the power adjusting section is composed of plural power levels, and the deficiency detecting section determines the amplification factor in accordance with an erasing power level that is used for erasing among the plural power levels.

* * * * *